United States Patent
Colombo et al.

(10) Patent No.: US 7,119,212 B2
(45) Date of Patent: Oct. 10, 2006

(54) PROCESS FOR THE PREPARATION OF TOLTERODINE AND INTERMEDIATES THEREOF

(75) Inventors: Lino Colombo, Pavia (IT); Roberto Rossi, Pavia (IT); Pietro Allegrini, San Donato Milanese (IT); Graziano Castaldi, Briona (IT)

(73) Assignee: Dipharma S.p.A., Mereto Di Tomba (IT)

( * ) Notice: Subject to any disclaimer, the term of this patent is extended or adjusted under 35 U.S.C. 154(b) by 0 days.

(21) Appl. No.: 11/092,553

(22) Filed: Mar. 29, 2005

(65) Prior Publication Data

US 2005/0222437 A1  Oct. 6, 2005

(30) Foreign Application Priority Data

Mar. 30, 2004  (IT)  .......................... MI2004A0616

(51) Int. Cl.
*C07D 311/20*  (2006.01)
*C07C 211/27*  (2006.01)

(52) U.S. Cl. ..................................... 549/290; 564/316
(58) Field of Classification Search ................ 549/290; 564/316

See application file for complete search history.

(56) References Cited

U.S. PATENT DOCUMENTS 6,310,248 B1 * 10/2001 Andersson et al. ......... 564/304

OTHER PUBLICATIONS

Defieber et al, Organic Letters, 6(21), pp. 3873-3876, Oct. 14, 2004.*

* cited by examiner

*Primary Examiner*—Bernard Dentz
(74) *Attorney, Agent, or Firm*—Young & Thompson

(57) ABSTRACT

A process for the preparation of 6-methyl-4-(R)-phenyl-chroman-2-one and 6-methyl-4-(S)-phenyl-chroman-2-one, intermediates for the synthesis of tolterodine and its (S) enantiomer, by reaction of 6-methyl-coumarin with phenyl-boronic acids, esters and derivatives thereof, in the presence of chiral catalysts.

19 Claims, No Drawings

PROCESS FOR THE PREPARATION OF TOLTERODINE AND INTERMEDIATES THEREOF

FIELD OF THE INVENTION

The present invention relates to a process for the preparation of tolterodine and intermediates thereof.

TECHNOLOGICAL BACKGROUND

Tolterodine (Xa), i.e. (R)-N,N-diisopropyl-3-(2-hydroxy-5-methylphenyl)-3-phenylpropanamine

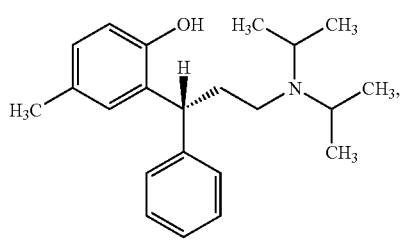

(Xa)

is a medicament useful in the treatment of urinary incontinence. U.S. Pat. No. 5,382,600 and U.S. Pat. No. 5,922,914 disclose a method for the preparation of tolterodine, which is isolated in the last step by resolution of the previously obtained racemic mixture. Andersson, Pher G. et al., *J. Org. Chem.* 1998, 63, pp. 8067–8070 and U.S. Pat. No. 6,310,248 disclose an enantioselective synthesis of tolterodine, which allows to avoid enantiomers separation. The (S) enantiomer of tolterodine, i.e. (S)-N,N-diisopropyl-3-(2-hydroxy-5-methylphenyl)-3-phenylpropanamine (Xb)

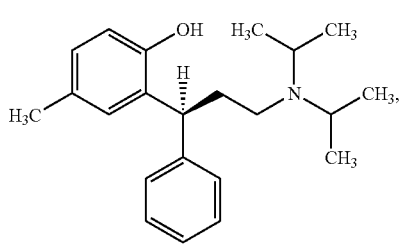

(Xb)

and its use in therapy are disclosed in WO 98/03067. In particular, in U.S. Pat. No. 6,310,248 the key step in the synthesis of tolterodine and of its (S) enantiomer is the preparation of 6-methyl-4-(R)-phenyl-chroman-2-one (Ia)

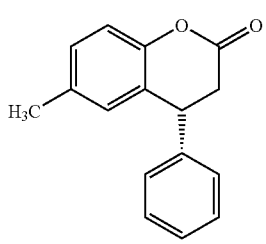

(Ia)

and 6-methyl-4-(S)-phenyl-chroman-2-one (Ib)

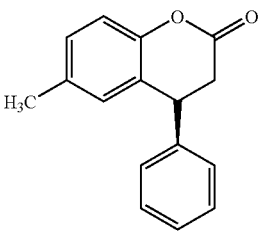

(Ib)

in enantiomerically enriched form by means of enantioselective reactions.

DETAILED DISCLOSURE OF THE INVENTION

It has now been found that 6-methyl-4-(R)-phenyl-chroman-2-one (Ia) and 6-methyl-4-(S)-phenyl-chroman-2-one (Ib) can be conveniently prepared by reaction of 6-methyl-coumarin with phenylboronic acids, their esters and derivatives, in the presence of chiral catalysts.

Accordingly, the present invention relates to a process for the preparation of 6-methyl-4-(R)-phenyl-chroman-2-one (Ia)

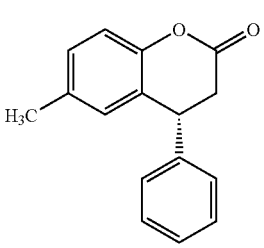

(Ia)

and 6-methyl-4-(S)-phenyl-chroman-2-one (Ib),

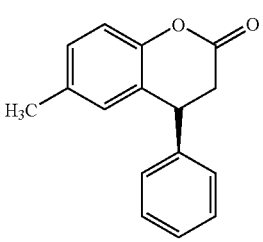

(Ib)

comprising the reaction of 6-methyl-coumarin (II)

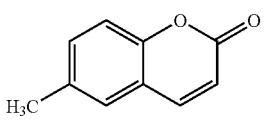

(II)

with a compound selected from those of formula (III), (IV), (V) and (VI)

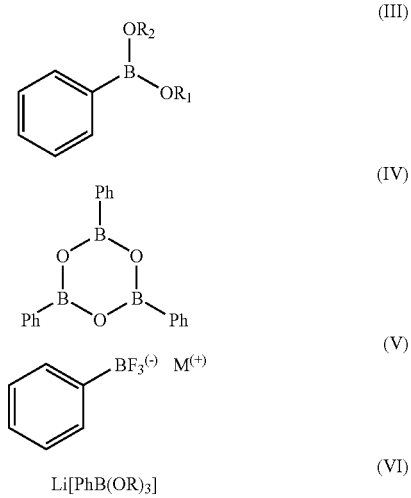

(III)
(IV)
(V)
(VI)

Li[PhB(OR)$_3$]

in the presence of a chiral catalyst.

In the compound of formula (III), each of $R_1$ and $R_2$, is independently a hydrogen atom, a $C_1$–$C_6$ alkyl group, an optionally substituted aryl or heteroaryl group; or $R_1$ and $R_2$, taken together, form a $C_2$–$C_6$ alkylene chain; or —$OR_1$ and —$OR_2$, taken together with the boron atom they are linked to, form a group of formula

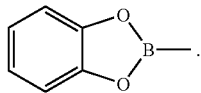

In the compounds of formula (IV) and (VI) Ph is phenyl; in the compound of formula (V) M$^+$ is a cation of a metal selected from Li, Na, K, Rb and Cs and in the compound of formula (VI) R is a $C_1$–$C_6$ alkyl group.

A $C_1$–$C_6$ alkyl group is a straight or branched alkyl group, preferably $C_1$–$C_4$ alkyl, in particular methyl, ethyl, propyl, i-propyl, n-butyl, sec-butyl or tert-butyl, more preferably methyl, ethyl or propyl.

A $C_2$–$C_6$ alkylene chain is a straight or branched chain, containing preferably 2 to 4 carbon atoms, in particular —CH$_2$—CH$_2$—, —CH$_2$—CH$_2$—CH$_2$—; —CH(CH$_3$)—CH$_2$—; —CH$_2$—CH(CH$_3$)—; —CH$_2$—CH(CH$_3$)—CH$_2$—; —CH(CH$_3$)—CH(CH$_3$)—and —CH$_2$—CH$_2$—CH$_2$—CH$_2$—.

An aryl group is for example phenyl or naphthyl, in particular phenyl, optionally substituted with one or more substituents, preferably from 1 to 3, independently selected from chlorine, bromine, iodine, fluorine, hydroxy, $C_1$–$C_4$ alkoxy, —SH, $C_1$–$C_4$ alkylthio, amino, mono- or di- $C_1$–$C_4$ alkylamino, nitro and cyano.

A heteroaryl group is a saturated or unsaturated heterocycle, monocyclic or bicyclic, optionally fused to one or two phenyl rings, containing one or more heteroatoms, preferably 1 to 3, independently selected from nitrogen, oxygen and sulfur, optionally substituted with one or more substituents, preferably from 1 to 3, independently selected from chlorine, bromine, iodine, fluorine, hydroxy, $C_1$–$C_4$ alkoxy, —SH, $C_1$–$C_4$ alkylthio, amino, mono- or di- $C_1$–$C_4$ alkylamino, nitro and cyano. Preferred examples of heteroaryl are furan, thiophene, pyrrole, pyridine, pyrazole, imidazole, oxazole, isoxazole, thiazole, benzofuran, dibenzofuran, thionaphthene, indole, quinoline, indazole, benzimidazole, pyridazine, pyrimidine, quinazoline, 1,2,4-triazole, 1,2,4-oxadiazole, 1,3,4-thiadiazole, purine and pteridine.

Preferred examples of compounds of formula (III) are phenyl boronic acid and its $C_1$–$C_4$ alkyl esters, such as phenyl dimethyl boronate, phenyl diisopropyl boronate, 5,5-dimethyl-2-phenyl-[1,3,2]dioxaborinane, in particular phenyl boronic acid.

A preferred example of compound of formula (V) is potassium phenyltrifluoroborate. A preferred example of compound of formula (VI) is lithium trimethyl phenylborate.

The chiral catalyst consists of a transition metal and a chiral ligand. Preferably, the transition metal is selected from Ni, Pd, Pt, Ru, Os, Ir and Rh, preferably rhodium. The transition metal can be added to the reaction mixture as salt or as oxide, but is preferably used as complex with organic ligands. Examples of organic ligands are the organic compounds able to form complexes with the metal thanks to the presence of nitrogen, oxygen, sulfur and phosphorous atoms or double and triple carbon-carbon bonds. Among nitrogen-containing organic ligands nitriles, such as acetonitrile and benzonitrile, amines and diamines such as 1,2-ethylenediamine, N,N'-dimethylethylenediamine and N,N,N',N'-tetramethylethylenediamine are preferred. Among oxygen-containing organic ligands alcohols, such as methanol, ethanol, n-propanol, isopropanol and tert-butanol, diols such as ethylene glycol, ketones such as acetone, methyl ethyl ketone, isobutyl methyl chetone, benzalacetone (4-phenyl-3-buten-2-one) and dibenzalacetone, diketones such as acetonylacetone, ethers such as ethyl ether, isopropyl ether, dioxane and tetrahydrofuran are preferred. Among sulfur-containing organic ligands sulfides, such as 2,5-dimethyl-tetrahydrothiophene, (1,11,11-trimethyl-6-p-tolyl-3-thiatricyclo[6.2.1.0$^{2,7}$]undec-5-yl)-methanol and 4,4,7-trimethyl-hexahydro-benzo[d][1,3]oxathiane are preferred. Among phosphorous-containing organic ligands mono- and bidentate phosphines, such as triphenylphosphine, tri-ortho-tolylphosphine, tributylphosphine, bisdiphenylphosphine methane, bisdiphenylphosphine ethane, bisdiphenylphosphine propane and bisdiphenylphosphine butane, further to phosphinites and diphosphonites in which the two oxygen atoms linked to the phosphorus atom are substituted with aromatic groups such as binaphthyl and phosphorus is linked to an aromatic residue are preferred. Among organic ligands that contain double and triple carbon-carbon bonds preferred examples are ethylene, 1,5-cyclooctadiene, cyclooctene and norbornadiene.

Preferred complexes of transition metals with organic ligands are rhodium acetylacetonate bisethylene (Rh(acac)(C$_2$H$_4$)$_2$), 1,5-cyclooctadiene bisacetonitrile rhodium tetrafluoborate (Rh(COD)(CH$_3$CN)$_2$BF$_4$), rhodium chloride cyclooctadiene [RhCl(COD)]$_2$ and rhodium hydroxy cyclooctadiene [RhOH(COD)]$_2$. Particularly preferred is 1,5-cyclooctadiene bisacetonitrile rhodium tetrafluoborate.

A chiral ligand, especially when optically pure, useful for the purposes of the present invention is a chiral molecule containing atoms able to form coordination bonds with transition metals. Examples of chiral ligands are phosphines, in particular Binap (2,2'-bis(diphenylphosphino)1,1'-binaphthyl) and diphosphonites such as dinaphtho[2,1-d:1',2'-f][1,3,2]dioxaphosphepin,4,4'-(1,2-ethanediyl)bis, dinaphtho[2,1-d:1',2'-f][1,3,2]dioxaphosphepin-4,4'-(1,2-butanediyl)bis and dinaphtho[2,1-d:1',2'-f][1,3,2]

dioxaphosphepin-4,4'-(1,2-phenylene)bis, phosphoroamidites such as those disclosed in the L1–L4 formulae by Minnaard et al. in Journal of Organic Chemistry, 2003, vol. 68, pages 9481–9484, diamines such as 1,2-cyclohexanediamine and C-pyrrolidin-2-yl-methylamine. Particularly preferred is Binap.

Depending on the configuration of the chiral ligand, a compound having absolute configuration (R) (compound (Ia)), or a compound having absolute configuration (S) (compound (Ib)) is obtained.

A preferred example of chiral ligand which affords a compound of formula (Ia) is (R)-(+)-Binap. A preferred example of chiral ligand which affords a compound of formula (Ib) is (S)-(−)-Binap.

Generally, compounds (III), (IV), (V) and (VI) are used in molar ratio ranging from 0.5 to 5, preferably from 1 to 3 with respect to 6-methyl-coumarin (II). The complex containing the transition metal with the organic ligand is generally used in ratio of 0.003–1 moles/mole of 6-methyl-coumarin, preferably 0.01–0.05 moles/mole. The optically pure chiral ligand is generally used in a ratio ranging from 0.5 to 3 moles/mole of compound containing the transition metal, preferably from 0.7 to 2 moles/mole. The reaction can be carried out in an organic solvent, for example selected from an aromatic hydrocarbon, in particular toluene, xylenes or isopropylbenzene; an aliphatic hydrocarbon, in particular n-hexane, cyclohexane or n-heptane; alkyl esters, in particular ethyl acetate, diisopropyl acetate or n-butyl acetate; ketones, in particular acetone, methyl ethyl ketone, methyl isobutyl ketone or cyclohexanone; ethers, in particular diethyl ether, dibutyl ether, diisopropyl ether, t-butylmethyl ether, 1-4-dioxane, tetrahydrofuran or 2-methyltetrahydrofuran; amides, in particular N,N-dimethylformamide, N,N-dimethylacetamide or 2-pyrrolidone; sulfoxides, in particular dimethylsulfoxide; sulfones, in particular sulfolane; an alcohol, in particular methanol, ethanol, isopropanol, n-butanol, 2-butanol, isobutanol or tert-butanol; or in water or mixtures of said organic solvents with or without water. The reaction is usually carried out a temperature ranging from about 0° C. to the reflux temperature of the solvent, preferably from about 20° C. to the reflux temperature. After completion of the reaction, the resulting product is recovered by conventional techniques known to those skilled in the art for the recovery of the organic compounds, for example chromatography on silica gel or crystallization from a suitable organic solvent. The compounds of formula (II), (III), (IV), (V) and (VI), as well as the chiral catalysts used to accomplish the invention, are compounds known and commercially available.

The advantages of the process of the invention compared with the known ones consist for example in that in a single step, starting from cheap commercially available compounds, the intermediates of formula (Ia) or (Ib) are obtained with the desired (R) or (S) absolute configuration, depending on the configuration of the chiral ligand, with high chemical purity and an at least 85% enantiomeric excess, preferably at least 99%. The quality of the resulting product allows the use of such product in the preparation of (R)- or (S)-tolterodine without the need of further purifications.

The conversion of the intermediates of formula (Ia) and (Ib) to tolterodine or (S)-tolterodine, or salts thereof, can be carried out according to what disclosed in U.S. Pat. No. 6,310,248, for example, by means of a process comprising:

a) the reaction of a compound of formula (Ia) or (Ib) with an amine of formula (VII)

HN(R$_3$R$_4$)        (VII)

wherein each of R$_3$ and R$_4$ is isopropyl, to give a compound of formula (VIIIa)

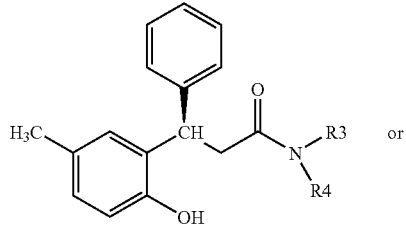

(VIIIa)

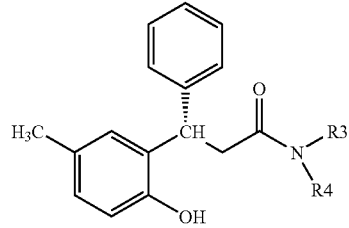

(VIIIb)

wherein R$_3$ and R$_4$ are as defined above; and b) the reduction of the carbamido group in the compounds (VIIIa) or (VIIIb) to give, respectively, tolterodine, or (S)-tolterodine, and the optional conversion to a salt thereof;

or by means of a process comprising a') the reduction of a compound of formula (Ia) or (Ib) to give a compound of formula (IXa)

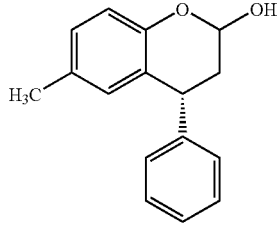

(IXa)

or

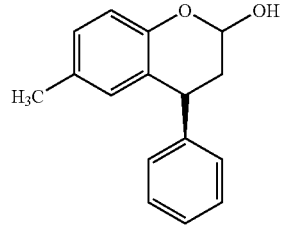

(IXb)

b') reductive amination of the hydroxy group in the compounds (IXa) and (IXb) with an amine of formula (VII) as defined above, to give, respectively, tolterodine, or (S)-tolterodine, and optional conversion to a salt thereof.

Therefore, a further object of the invention is a process for preparation of tolterodine or of (S)-tolterodine, or salts thereof, comprising the use of compounds of formula (Ia) or (Ib) obtained as described above.

The following examples illustrate a preferred embodiment of the invention.

EXAMPLES

Example 1

Preparation of 6-methyl-4-(R)-phenyl-dihydrocumarin

[Rh(Cod)(MeCN)$_2$]BF$_4$ (0.03 mmoles, 10.7 mg), (R)-(+)-Binap (0.04 mmoles, 26.2 mg) and phenylboronic acid (2.95 mmoles, 342.6 mg) are introduced in succession in a 25 ml round-bottom flask, equipped with magnetic stirrer, condenser and kept under N$_2$ atmosphere. Thereafter, 4 ml of distilled dioxane are added and the solution is kept under magnetic stirring for 30', then a solution of 6-methyl-coumarin (0.94 mmoles, 150 mg) in dioxane (1.6 ml) containing Et$_3$N (0.94 mmoles, 94.7 mg, d=0.727) is added and the mixture is heated at 70° C. for 45'. After 45' dioxane is evaporated off under reduced pressure, to obtain a burgundy solid, which is diluted with ethyl acetate and added with 6 ml of a NH$_4$Cl saturated aqueous solution. The organic phase is separated, whereas the aqueous phase is extracted three times with ethyl acetate. The combined organic phases are dried over sodium sulfate and evaporated under reduced pressure. The resulting crude mixture (275 mg) is purified by flash chromatography on silica gel (eluant 96:4 v/v hexane:ethyl acetate). 93.7 mg of 6-methyl-4-(R)-phenyl-dihydrocumarin are obtained as a white solid (molar yield 42%).

Enantiomeric excess (calculated by HPLC analysis under the conditions disclosed in U.S. Pat. No. 6,310,248): 98.1%. [α]$_D$=−3.1 (c=0.96, CDCl$_3$, R.T.).

Example 2

Preparation of 6-methyl-4-(R)-phenyl-dihydrocumarin

[Rh(Cod)(MeCN)$_2$]BF$_4$ (0.03 mmoles, 10.7 mg), (R)-(+)-Binap (0.04 mmoles, 26.24 mg) and phenylboronic acid (2.9 mmoles, 342.6 mg) are introduced in succession in a 25 ml round-bottom flask, equipped with magnetic stirrer, condenser and kept under N$_2$ atmosphere. After addition of 4 ml of t-butyl alcohol the suspension is kept under magnetic stirring for 30'. The resulting mixture is added with a solution of 6-methyl-coumarin (0.94 mmoles, 150 mg) in t-butyl alcohol (1.6 ml) containing Et$_3$N (0.94 mmoles, 94.8 mg) and is heated at 60° C.–70° C. for 2 hours 20 minutes. t-Butyl alcohol is evaporated off under reduced pressure, to obtain a burgundy solid, which is diluted with ethyl acetate and added with 6 ml of a NH$_4$Cl saturated aqueous solution. The aqueous phase is separated and extracted three times with ethyl acetate. The four combined organic phases are dried over sodium sulfate, filtered and evaporated under reduced pressure.

The resulting crude mixture is purified by flash chromatography on silica gel (eluant 96:4 v/v hexane:ethyl acetate).

161 mg of 6-methyl-4-(R)-phenyl-dihydrocumarin are obtained as a white solid (yield: 72.0%). Enantiomeric excess (calculated by HPLC analysis under the conditions described in U.S. Pat. No. 6,310,248): 68%.

Example 3

Preparation of 6-methyl-4-(S)-phenyl-dihydrocumarin

[Rh(Cod)(MeCN)$_2$]BF$_4$ (0.06 mmoles, 21.4 mg), (S)-(−)-Binap (0.08 mmoles, 52.5 mg) and phenylboronic acid (5.6 mmoles, 685.1 mg) are introduced in succession in a 50 ml round-bottom flask, equipped with magnetic stirrer, condenser and kept under N$_2$ atmosphere. After addition of 5 ml of distilled dioxane the solution is kept under magnetic stirring for 30', then added with a solution of 6-methyl-coumarin (1.87 mmoles, 300 mg) in dioxane (6 ml) containing Et$_3$N (1.9 mmoles, 189.5 mg) and heated at 70° C. for 45'. After 45' dioxane is evaporated off under reduced pressure, thereby obtaining a burgundy solid, which is diluted with ethyl acetate and added with 6 ml of a NH$_4$Cl saturated aqueous solution. The organic phase is separated, the aqueous phase is extracted three times with ethyl acetate. The combined organic phases are dried over sodium sulfate and evaporated under reduced pressure.

The resulting crude mixture is purified by flash chromatography on silica gel (eluant 96:4 v/v hexane:ethyl acetate).

201 mg of 6-methyl-4-(R)-phenyl-dihydrocumarin are obtained as a white solid (molar yield: 45%).

Enantiomeric excess (calculated by HPLC analysis under the conditions disclosed in U.S. Pat. No. 6,310,248): 98.4%. [α]$_D$=+2.8 (c=0.96, CDCl$_3$, R.T.).

The invention claimed is:

1. A process for the preparation of 6-methyl-4-(R)-phenyl-chroman-2-one (Ia)

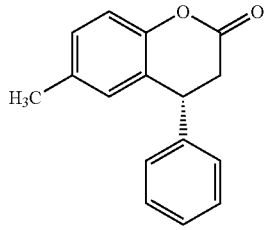

(Ia)

or 6-methyl-4-(S)-phenyl-chroman-2-one (Ib),

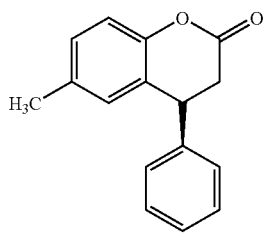

(Ib)

comprising the reaction of 6-methyl-coumarin (II)

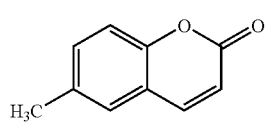

(II)

with a compound selected from the group consisting of formulae (III), (IV), (V), and (VI)

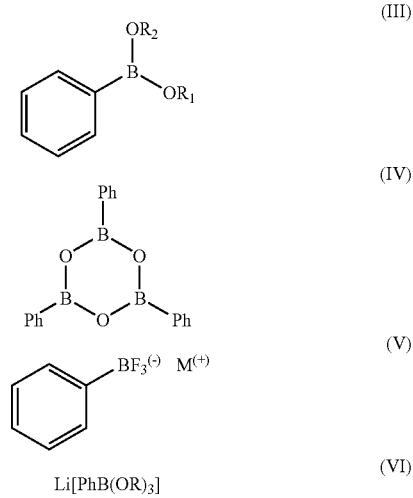

in the presence of a chiral catalyst, in which:
in the compound of formula (III), each of $R_1$ and $R_2$ is independently a hydrogen atom, a $C_1$–$C_6$ alkyl group, an optionally substituted aryl or heteroaryl group; or $R_1$ and $R_2$, taken together, form a $C_2$–$C_6$ alkylene chain; or —$OR_1$ and —$OR_2$, taken together with the boron atom they are linked to, form a group of formula

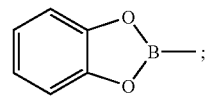

in the compounds of formula (IV) and (VI) Ph is phenyl;
in the compound of formula (V) $M^+$ is a metal cation selected from Li, Na, K, Rb and Cs; and
in the compound of formula (VI) R is a $C_1$–$C_6$ alkyl group.

2. The process as claimed in claim 1, wherein the chiral catalyst consists of a transition metal and a chiral ligand.

3. The process as claimed in claim 2, wherein the transition metal is used as complex with organic ligands.

4. The process according to claim 3, wherein the complex of the transition metal with an organic ligand is selected from rhodium acetylacetonate bisethylene, 1,5-cyclooctadiene bisacetonitrile rhodium tetrafluoborate, rhodium chloride cyclooctadiene and rhodium hydroxy cyclooctadiene.

5. The process as claimed in claim 2, wherein the chiral ligand is selected from a phosphine, a diphosphonite, a phosphoramidite and a diamine.

6. The process according to claim 1, wherein the compound of formula (III), (IV), (V) or (VI) is used in a molar ratio ranging from 0.5 to 5 with respect to 6-methyl-coumarin.

7. The process according to claim 1, wherein the complex containing the transition metal with the organic ligand is used in a ratio of 0.003–1 moles/mole of 6-methyl-coumarin (II).

8. The process according to claim 1, wherein the chiral ligand is used in a ratio ranging from 0.5 to 3 moles/mole of compound containing the transition metal.

9. A process for the preparation of (R)—N,N-diisopropyl-3-(2-hydroxy-5-methylphenyl)-3-phenyipropanamine or (S)—N,N-diisopropyl-3-(2-hydroxy-5-methyiphenyl)-3-phenyipropanamine, or the salts thereof, comprising the use of a compound of at least one of 6-methyl-4-(R)-phenyl-chroman-2-one (Ia)

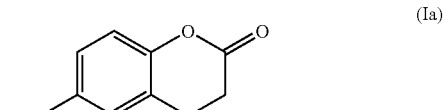

or 6-methyl-4-(S)-phenyl-chroman-2-one (Ib),

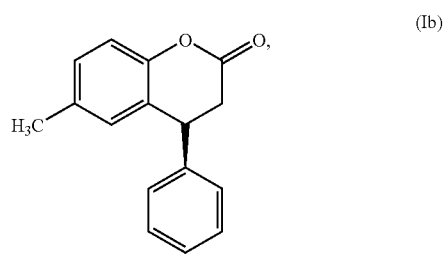

wherein said compound is obtained according to the process of claim 1.

10. The process according to claim 2, wherein the compound of formula (III), (IV), (V) or (VI) is used in a molar ratio ranging from 0.5 to 5 with respect to 6-methyl-coumarin.

11. The process according to claim 3, wherein the compound of formula (III), (IV), (V) or (VI) is used in a molar ratio ranging from 0.5 to 5 with respect to 6-methyl-coumarin.

12. The process according to claim 4, wherein the compound of formula (ITT), (IV), CV) or (VI) is used in a molar ratio ranging from 0.5 to 5 with respect to 6-methyl-coumarin.

13. The process according to claim 5, wherein the compound of formula (III), (IV), (V) or (VI) is used in a molar ratio ranging from 0.5 to 5 with respect to 6-methyl-coumarin.

14. The process according to claim 2, wherein the complex containing the transition metal with the organic ligand is used in a ratio of 0.003–1 moles/mole of 6-methyl-coumarin (II).

15. The process according to claim 3, wherein the complex containing the transition metal with the organic ligand is used in a ratio of 0.003–1 moles/mole of 6-methyl-coumarin (II).

16. The process according to claim 4, wherein the complex containing the transition metal with the organic ligand is used in a ratio of 0.003–1 moles/mole of 6-methyl-coumarin (II).

17. The process according to claim 5, wherein the complex containing the transition metal with the organic ligand is used in a ratio of 0.003–1 moles/mole of 6-methyl-coumarin (II).

18. The process according to claim 6, wherein the complex containing the transition metal with the organic ligand is used in a ratio of 0.003–1 moles/mole of 6-methyl-coumarin (II).

19. The process according to claim 2, wherein the chiral ligand is used in a ratio ranging from 0.5 to 3 moles/mole of compound containing the transition metal.

* * * * *